US00PP31657P2

(12) United States Plant Patent
Westervelt

(10) Patent No.: US PP31,657 P2
(45) Date of Patent: Apr. 14, 2020

(54) WHITE SPRUCE TREE NAMED 'CHARLIE J. NICKEL'

(50) Latin Name: ***Picea glauca* var. *densata***
Varietal Denomination: Charlie J. Nickel

(71) Applicant: Keith D. Westervelt, Manhattan, KS (US)

(72) Inventor: Keith D. Westervelt, Manhattan, KS (US)

( * ) Notice: Subject to any disclaimer, the term of this patent is extended or adjusted under 35 U.S.C. 154(b) by 0 days.

(21) Appl. No.: 16/501,175

(22) Filed: Mar. 1, 2019

(51) Int. Cl.
*A01H 7/00* (2006.01)
*A01H 6/00* (2018.01)

(52) U.S. Cl.
USPC ..... Plt./213
CPC ..... *A01H 6/00* (2018.05)

(58) Field of Classification Search
USPC ..... Plt./213
See application file for complete search history.

*Primary Examiner* — Anne Marie Grunberg
(74) *Attorney, Agent, or Firm* — Penny J. Aguirre

(57) ABSTRACT

A new cultivar of white spruce tree named 'Charlie J. Nickel' that is characterized by its needles that are tinted blue in color, its uniform ovate-shaped plant habit with a strong central leader, and its good growth rate.

2 Drawing Sheets

Botanical classification: *Picea glauca* var. *densata*.
Varietal denomination: 'Charlie J. Nickel'.

BACKGROUND OF THE INVENTION

The present invention relates to a new and distinct cultivar of *Picea glauca* var. *densata* and will be referred to hereafter by its cultivar name, 'Charlie J. Nickel'. 'Charlie J. Nickel' represents a new cultivar of black hills white spruce, an evergreen plant grown for landscape use.

The inventor discovered 'Charlie J. Nickel' as a chance seedling in March of 2001 that was growing in a row of unnamed plants of *Picea glauca* var. *densata* that had been lined out in a field plot at his nursery in Manhattan, Kans. The parent plants are therefore unknown. The instant plant may be referred to as a white spruce, a black hills white spruce, or a black hills spruce.

Asexual propagation of the new cultivar was first accomplished by grafting onto Norway Spruce rootstock in McMinnville, Oreg. in January of 2002 under the direction of the Inventor. Asexual propagation by grafting has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Charlie J. Nickel' as a unique cultivar of black hills spruce.

1. 'Charlie J. Nickel' exhibits needles that are tinted blue in color.
2. 'Charlie J. Nickel' exhibits a uniform ovate-shaped plant habit with a strong central leader.
3. 'Charlie J. Nickel' exhibits a good growth rate.

The unnamed plants of *Picea glauca* var. *densata* that were growing in the area of discovery differ from 'Charlie J. Nickel' in having foliage that is greener in color, in lacking a uniform in shape, and in having a slower growth rate.

'Charlie J. Nickel' can be most closely compared to the *Picea glauca* var. *densata* cultivars 'Westervelt' (U.S. Plant Pat. No. 29,825) and 'Wiskey Blue Hills' (not patented). 'Westervelt' is similar to 'Charlie J. Nickel' in having blue tinted foliage and in growth rate but differs from 'Charlie J. Nickel' in having a narrow plant habit. 'Wiskey Blue Hills' is similar to 'Charlie J. Nickel' in having blue foliage but differs from 'Charlie J. Nickel' in having a slower growth rate, a more pyramidal and semi-compact plant habit with a smaller mature plant size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The plant and plant parts depicted in the accompanied photographs illustrate the characteristics of 'Charlie J. Nickel'. The photographs were taken of 26-year-old plants as grown in the ground in Manhattan, Kans.

The photograph in FIG. 1 provides a view of the plant habit of 'Charlie J. Nickel'.

Figure 1:
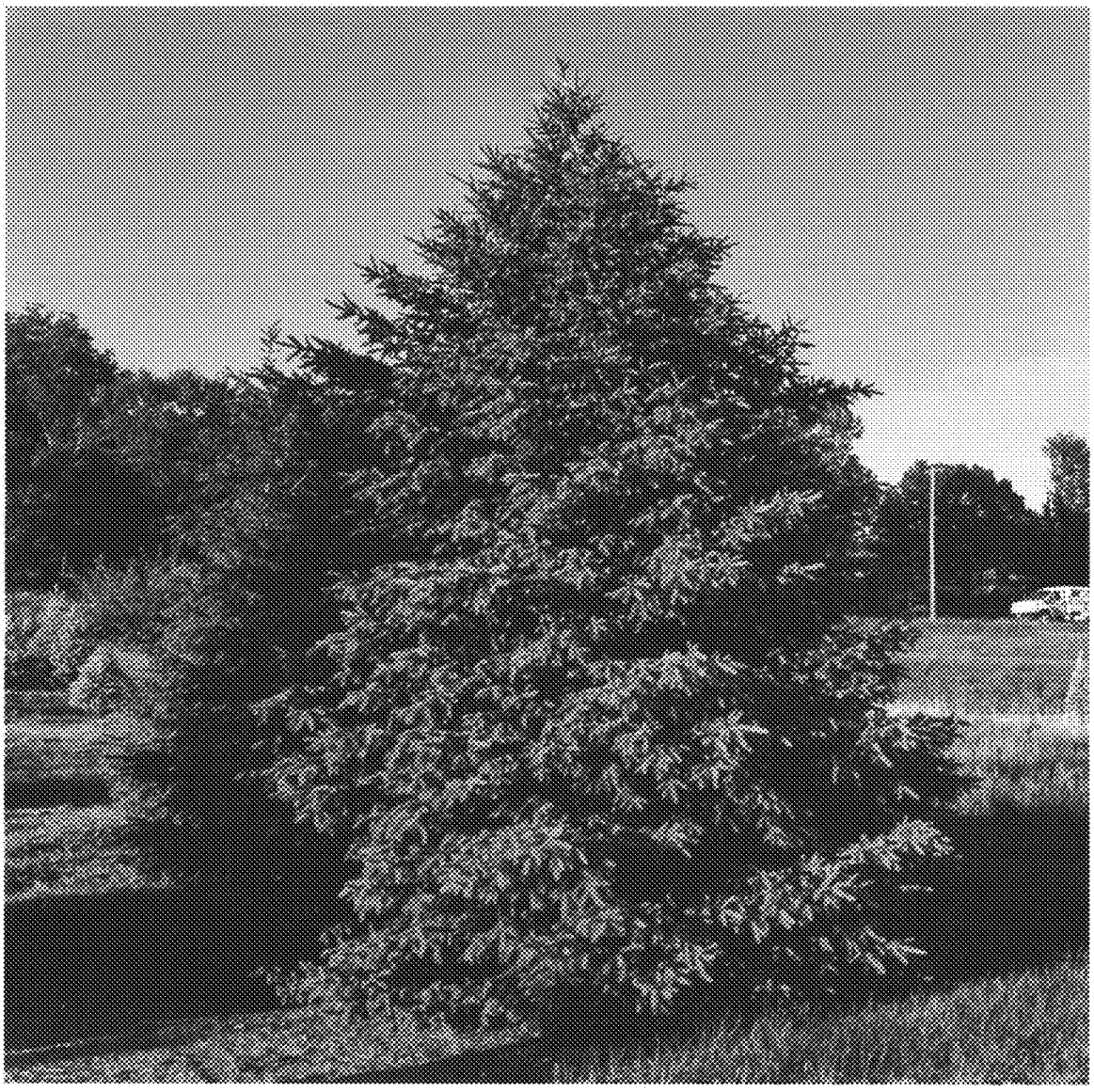
Figure 2:
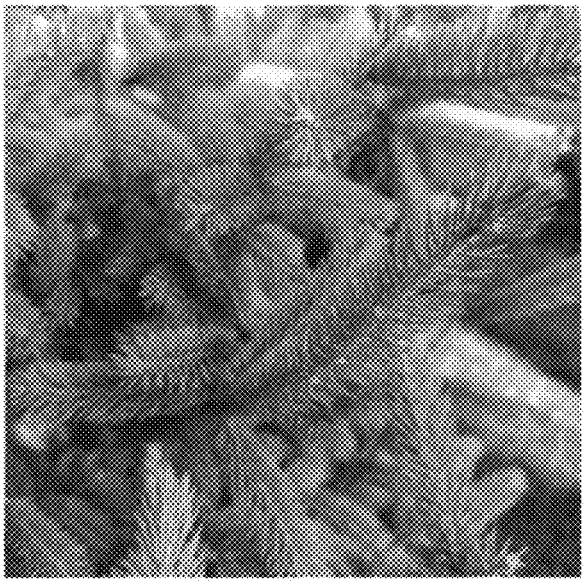

The photograph in FIG. 2 provides a close-up view of the foliage of 'Charlie J. Nickel'.

Figure 3:
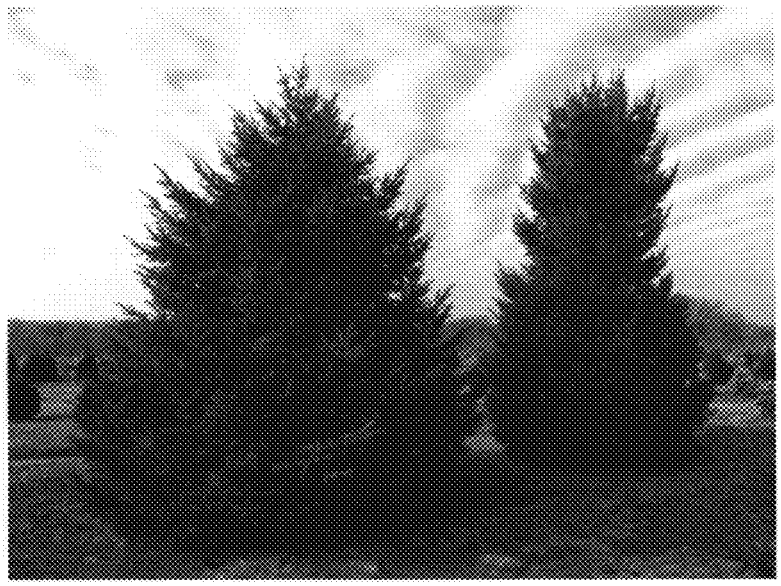

The photograph in FIG. 3 provides a comparison between trees of 'Charlie J. Nickel' on the left and 'Westervelt' on the right.

The colors in the photographs are as close as possible with the photographic and printing technology utilized. The color values cited in the detailed botanical description accurately describe the colors of the new *Picea*.

DETAILED BOTANICAL DESCRIPTION

The following is a detailed description of the new cultivar as taken from 2-year-old trees as grown outdoors in 1-gallon containers in McMinnville, Oreg. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Coniferous, evergreen for landscape use.

*Growth habit.*—Uniform, ovate-shaped.

*Height and spread.*—An average of 12 m height and width (at base) for a tree ten years in age.

*Hardiness.*—At least in U.S.D.A. Zones 2 to 6.

*Diseases and pests.*—No susceptibility or resistance to pests or diseases has been observed.

*Root description.*—Fibrous, moderately branched, moderately thick, a blend of N199B and N199C in color.

*Growth rate.*—Good for plants of the species, an average of 15 cm per year.

*Propagation.*—Grafting.

*Time to graft a young plant.*—About 6 to 8 weeks to graft onto 1-year-old Norway Spruce rootstock.

Branch description:

*Trunk and branch shape.*—Rounded.

*Branch size.*—Main trunk; 95 cm in length, 2.5 cm in diameter measured 2 cm from soil level, lateral branches; average of 60 cm in length, up to 1.5 cm in width, tertiary branches; up to 35 cm in length, 7 mm in width.

*Stem surface.*—Main and lateral branches; finely covered with bark and covered with lenticels; raised, 15 per 2 cm×2 cm, 200A in color.

*Branching.*—Average of 19 lateral branches, 4 to 6 tertiary branches per lateral, strong central leader.

*Stem arrangement.*—Main branches; whorled, irregular, lateral branches; opposite.

*Stem aspect.*—Strong, held at an average angle of 45° or less.

*Internode length.*—Average of 4 cm.

*Stem color.*—One year-old stems; 161B, mature bark; close to 201A with slight undertones of N199B.

*Resin glands.*—None observed.

Foliage description:

*Leaf arrangement.*—Densely whorled needles.

*Leaf attachment.*—Sessile.

*Leaf shape.*—Linear, scale-like, obliquely pointed.

*Leaf division.*—Simple.

*Leaf base.*—Truncate

*Leaf apex.*—Oblique.

*Leaf venation.*—Not visible.

*Leaf margins.*—Entire.

*Leaf fragrance.*—When crushed, it produces a pine-like fragrance.

*Leaf surface and texture.*—Young upper and lower surfaces; glabrous, glossy, mature upper and lower surfaces; glabrous, matte.

*Leaf color.*—Young; 145A, mature; a blend of 139A and 139B.

*Leaf size.*—An average of 1.5 cm in length and 1 mm in diameter.

*Leaf quantity.*—Average of 130 per branchlet 15 cm in length.

*Leaf buds.*—1 cm in length and 5 mm in diameter, a blend of 166A in color, comprised of imbricate scales orbicular and cupped in shape and average of 2 mm in length and width, glossy surface, pointed apex, narrow oblong in shape, average of 6 per 15 cm branchlet.

Cone description: None observed at date.

It is claimed:

1. A new and distinct cultivar of white spruce tree named 'Charlie J. Nickel' as herein illustrated and described.

* * * * *